(12) United States Patent
Yoo et al.

(10) Patent No.: US 10,709,893 B2
(45) Date of Patent: *Jul. 14, 2020

(54) SYSTEM AND METHOD FOR PROVIDING FLUID REAL-TIME VISUALIZATION OF REGION OF TISSUE ACTIVATION

(71) Applicant: Boston Scientific Neuromodulation Corporation, Valencia, CA (US)

(72) Inventors: Peter J. Yoo, Burbank, CA (US); Michael A. Moffitt, Saugus, CA (US); Kerry Bradley, Glendale, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 63 days.

This patent is subject to a terminal disclaimer.

(21) Appl. No.: 15/859,119

(22) Filed: Dec. 29, 2017

(65) Prior Publication Data

US 2018/0140854 A1 May 24, 2018

Related U.S. Application Data

(63) Continuation of application No. 13/244,415, filed on Sep. 24, 2011, now Pat. No. 9,855,432.

(Continued)

(51) Int. Cl.
*A61N 1/36* (2006.01)
*A61N 1/372* (2006.01)

(52) U.S. Cl.
CPC ..... *A61N 1/37247* (2013.01); *A61N 1/36185* (2013.01); *A61N 1/36135* (2013.01)

(58) Field of Classification Search
CPC ............ A61N 1/36135; A61N 1/36185; A61N 1/37247

See application file for complete search history.

(56) References Cited

U.S. PATENT DOCUMENTS 6,516,227 B1 2/2003 Meadows et al.
6,895,280 B2 5/2005 Meadows et al.
(Continued)

FOREIGN PATENT DOCUMENTS

WO WO 2007/097873 8/2007
WO WO 2008/005142 1/2008
(Continued)

OTHER PUBLICATIONS

Brief Communication for European Patent Application 11767546.2 dated Aug. 29, 2017 from the European Patent Office (7 pages).
PCT International Preliminary Report on Patentability (Chapter I of the Patent Cooperation Treaty) for PCT/US11/053174, Applicant: Boston Scientific Neuromodulation Corporation, Form PCT/IB/326 and 373, dated May 10, 2013 (7 pages).
(Continued)

*Primary Examiner* — Eric D. Bertram
(74) *Attorney, Agent, or Firm* — Lowe Graham Jones PLLC; Bruce E. Black

(57) ABSTRACT

A system for a tissue stimulator coupled to an array of electrodes. The system comprises a user-controlled input device configured for generating control signals, and at least one processor configured for generating a plurality of stimulation parameter sets in response to the control signals that, when applied to the electrodes, will shift electrical current between electrodes to modify a region of tissue activation. The processor(s) is further configured for computing an estimate of the region of tissue activation, and for generating display signals capable of prompting a monitor to display an animated graphical representation of the computed estimate of the region of tissue activation.

20 Claims, 17 Drawing Sheets

Related U.S. Application Data

(60) Provisional application No. 61/407,689, filed on Oct. 28, 2010.

(56) References Cited

U.S. PATENT DOCUMENTS

| | | | |
|---|---|---|---|
| 6,993,384 | B2 | 1/2006 | Bradley et al. |
| 7,623,918 | B2 | 11/2009 | Goetz |
| 7,650,184 | B2 | 1/2010 | Walter |
| 8,019,439 | B2 | 9/2011 | Kuzma et al. |
| 2007/0168004 | A1 | 7/2007 | Walter |
| 2007/0168007 | A1 | 7/2007 | Kuzma et al. |
| 2007/0203543 | A1* | 8/2007 | Stone ............... A61N 1/37247 607/59 |
| 2008/0154340 | A1* | 6/2008 | Goetz ............... A61N 1/36185 607/59 |
| 2008/0215118 | A1 | 9/2008 | Goetz et al. |
| 2008/0215119 | A1 | 9/2008 | Woods et al. |
| 2009/0287272 | A1* | 11/2009 | Kokones ............ A61N 1/37247 607/45 |
| 2010/0010566 | A1 | 1/2010 | Thacker et al. |
| 2010/0121409 | A1 | 5/2010 | Kothandaraman et al. |
| 2011/0040546 | A1 | 2/2011 | Gerber et al. |

FOREIGN PATENT DOCUMENTS

| | | |
|---|---|---|
| WO | WO 2009/134475 | 11/2009 |
| WO | WO 20111085206 | 1/2011 |
| WO | WO 20111136870 | 11/2011 |
| WO | WO 20111156581 | 12/2011 |

OTHER PUBLICATIONS

PCT International Search Report for PCT/US2011/053174, Applicant: Boston Scientific Neuromodulation Corporation, Form PCT/ISA/210 and 220, dated Mar. 16, 2012 (5 pages).

PCT Written Opinion of the International Search Authority for PCT/US2011/053174, Applicant: Boston Scientific Neuromodulation Corporation, Form PCT/ISA/237, dated Mar. 16, 2012 (5 pages).

Hunka. Karen. et al.. Nursing Time to Program and Assess Deep Brain Stimulators in Movement Disorder Patients. J. Neursci Nurs., Aug. 2005,37,4,204-10.

Frankemolle, Ann Eke M.M., et al., Reversing cognitive-motor impairments in Parkinson's disease patients using a computational modelling approach to deep brain stimulation programming, Brain 2010,133,746-761.

U.S. Appl. No. 611374,879, Entitled: User Interface for Segmented Neurostimulation Leads, Inventor: Michael A. Moffitt, et al., filed: Aug. 18, 2010.

Official Communication for U.S. Appl. No. 13/244,415 dated Apr. 28, 2017.

Official Communication for U.S. Appl. No. 13/244,415 dated Nov. 23, 2016.

Official Communication for U.S. Appl. No. 13/244,415 dated Jul. 22, 2013.

Official Communication for U.S. Appl. No. 13/244,415 dated Feb. 28, 2013.

U.S. Appl. No. 13/244,415, filed Sep. 24, 2011.

\* cited by examiner

SYSTEM AND METHOD FOR PROVIDING FLUID REAL-TIME VISUALIZATION OF REGION OF TISSUE ACTIVATION

RELATED APPLICATION

The present application is a continuation of U.S. patent application Ser. No. 13/244,415, filed Sep. 24, 2011, now U.S. Pat. No. 9,855,432, which claims the benefit under 35 U.S.C. § 119 to U.S. provisional patent application Ser. No. 61/407,689, filed Oct. 28, 2010. The foregoing applications are hereby incorporated by reference into the present application in their entirety.

FIELD OF THE INVENTION

The present invention relates to tissue stimulation systems, and more particularly, to neurostimulation systems and method of simulating the region of tissue activation.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoris and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems such as the Freehand system by NeuroControl (Cleveland, Ohio) have been applied to restore some functionality to paralyzed extremities in spinal cord injury patients. Furthermore, in recent investigations Peripheral Nerve Stimulation (PNS) systems have demonstrated efficacy in the treatment of chronic pain syndromes and incontinence, and a number of additional applications are currently under investigation. Occipital Nerve Stimulation (ONS), in which leads are implanted in the tissue over the occipital nerves, has shown promise as a treatment for various headaches, including migraine headaches, cluster headaches, and cervicogenic headaches.

Each of these implantable neurostimulation systems typically includes one or more electrode carrying stimulation leads, which are implanted at the desired stimulation site, and a neurostimulator implanted remotely from the stimulation site, but coupled either directly to the neurostimulation lead(s) or indirectly to the neurostimulation lead(s) via a lead extension. The neurostimulation system may further comprise a handheld external control device to remotely instruct the neurostimulator to generate electrical stimulation pulses in accordance with selected stimulation parameters. Typically, the stimulation parameters programmed into the neurostimulator can be adjusted by manipulating controls on the external control device to modify the electrical stimulation provided by the neurostimulator system to the patient.

The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero.

With some neurostimulation systems, e.g., those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

Other parameters that may be controlled or varied include the amplitude, width, and rate of the electrical pulses provided through the electrode array. Each electrode combination, along with the electrical pulse parameters, can be referred to as a "stimulation parameter set."

Thus, stimulation parameters programmed into the neurostimulator can be adjusted by manipulating controls on the external control device to modify the electrical stimulation provided by the neurostimulator system to the patient. In accordance with the stimulation parameters programmed by the external control device, electrical pulses can be delivered from the neurostimulator to the stimulation electrode(s) to stimulate or activate a region of tissue in accordance with a set of stimulation parameters and provide the desired efficacious therapy to the patient.

Significantly, non-optimal electrode placement and stimulation parameter selections may result in excessive energy consumption due to stimulation that is set at too high an amplitude, too wide a pulse duration, or too fast a frequency; inadequate or marginalized treatment due to stimulation that is set at too low an amplitude, too narrow a pulse duration, or too slow a frequency; or stimulation of neighboring cell populations that may result in undesirable side effects.

For example, in the context of DBS, bilateral stimulation of the subthalamic nucleus has been proven to provide effective therapy for improving the major motor signs of advanced Parkinson's disease, and although the bilateral stimulation of the subthalamic nucleus is considered safe, an emerging concern is the potential negative consequences that it may have on cognitive functioning and overall quality of life (see A. M. M. Frankemolle, et al., *Reversing Cognitive-Motor Impairments in Parkinson's Disease Patients Using a Computational Modelling Approach to Deep Brain Stimulation Programming*, Brain 2010; pp. 1-16). In large part, this phenomenon is due to the small size of the subthalamic nucleus. Even with the electrodes are located predominately within the sensorimotor territory, the electrical field generated by DBS is non-discriminately applied to all neural elements surrounding the electrodes, thereby resulting in the spread of current to neural elements affecting cognition. As a result, diminished cognitive function during stimulation of the subthalamic nucleus may occur do to non-selective activation of non-motor pathways within or around the subthalamic nucleus.

Thus, the best stimulus parameter set will typically be one that delivers stimulation energy to the region of tissue that must be stimulated in order to provide the therapeutic benefit, while minimizing the region of non-target tissue that is stimulated. However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate, selection of optimal stimulation parameter sets, the clinician generally programs the external control device, and if applicable the neurostimulator, through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback and to subsequently program the external control device with the optimum stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. Once the leads are correctly positioned, a fitting procedure, which may be referred to as a navigation session, may be performed using the computerized programming system to program the external control device, and if applicable the neurostimulator, with a set of stimulation parameters that best addresses the neurological disorder(s).

Thus, the navigation session may be used to pinpoint the stimulation region or areas correlating to the disease to be treated. Such programming ability may be advantageous for targeting the tissue during implantation, or after implantation should the leads gradually or unexpectedly move that would otherwise relocate the stimulation energy away from the target site, if the body adapts to the specific stimulation parameters currently programmed into a neurostimulation system, or the full effects of stimulation are not manifest in a short period of time (i.e., not observed within a programming session).

By reprogramming the neurostimulator (typically by independently varying the stimulation energy on the electrodes), the stimulation region can often be moved back to the targeted tissue site without having to re-operate on the patient in order to reposition the lead and its electrode array. When adjusting the stimulation region relative to the tissue, it is desirable to make small changes in the proportions of current, so that changes in the spatial recruitment of nerve fibers will be smooth and continuous and to have incremental targeting capability.

One known computerized programming system for neurostimulation is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes, or may be operated by the clinician in an "automated mode" to electrically "steer" the current along the implanted leads in real-time (e.g., using a joystick or joystick-like controls), thereby allowing the clinician to determine the most efficacious stimulation parameter sets that can then be stored and eventually combined into stimulation programs.

Regardless of the skill of the physician or clinician, neurostimulation programming sessions can be especially lengthy when programming complicated neurostimulation systems, such as DBS systems, where patient usually cannot feel the effects of stimulation, and the effects of the stimulation may be difficult to observe, are typically subjective, or otherwise may take a long time to become apparent. Clinical estimates suggest that 10-36 hours per patient are necessary to program and assess DBS patients with current techniques (see Hunka K., et al., *Nursing Time to Program and Assess Deep Brain Stimulators in Movement Disorder Patients*, J. Neursci Nurs. 37: 204-10), which is an extremely large time commitment for both the physician/clinician and the patient.

There, thus, remains a need for a user interface that more efficiently allows the programming of neurostimulation systems.

SUMMARY OF THE INVENTION

In accordance with the present inventions, a system for a neurostimulator coupled to an array of electrodes is provided.

The system comprises a user-controlled input device configured for generating control signals. In one embodiment, the user-control input device includes a control element, a continual actuation of which generates the control signals. The control signals may be directional control signals. In this case, the user-control input device may be, e.g., one or more of a graphical arrow, a joystick, a touchpad, a button pad, a group of keyboard arrow keys, a mouse, a roller ball tracking device, and horizontal and vertical rocker-type arm switches.

The system further comprises at least one processor configured for generating a plurality of stimulation parameter sets in response to the control signals that, when applied to the electrodes, will shift electrical current (e.g., cathodic electrical current) between the electrodes to modify a region of tissue activation. For example, if the array of electrodes is a one-dimensional array of electrodes, and the processor(s) may be configured for generating the plurality of stimulation parameter sets in response to the control signals that, when applied to the electrodes, will shift the electrical current up and down in one dimension. If the array of electrodes is a two-dimensional array of electrodes, the processor(s) may be configured for generating the plurality of stimulation parameter sets in response to the control signals that, when applied to the electrodes, will shift the electrical current in two dimensions. If the array of electrodes is a three-dimensional array of electrodes, the processor(s) may be configured for generating the plurality of stimulation parameter sets in response to the control signals that, when applied to the electrodes, will shift the electrical current in three dimensions.

The processor(s) is further configured for computing an estimate of the region of tissue activation, and for generating display signals capable of prompting a monitor to display an animated graphical representation of the computed estimate of the region of tissue activation, which may be three-dimensional. For example, a shape of the animated graphical representation may change, a locus position of the animated graphical representation may change, a size of the animated graphical representation may change, a shade of the animated graphical representation changes, a transparency of the animated graphical representation may change, and/or a color of the animated graphical representation may change.

In an optional embodiment, the system further comprises telemetry circuitry, in which case, the processor(s) may be further configured for programming at least one of the neurostimulation parameter sets via the telemetry circuitry.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a spinal cord stimulator, peripheral nerve stimulator, microstimulator, or in any other neural stimulator configured to treat urinary incontinence, sleep apnea, shoulder subluxation, headache, etc.

Figure 1:
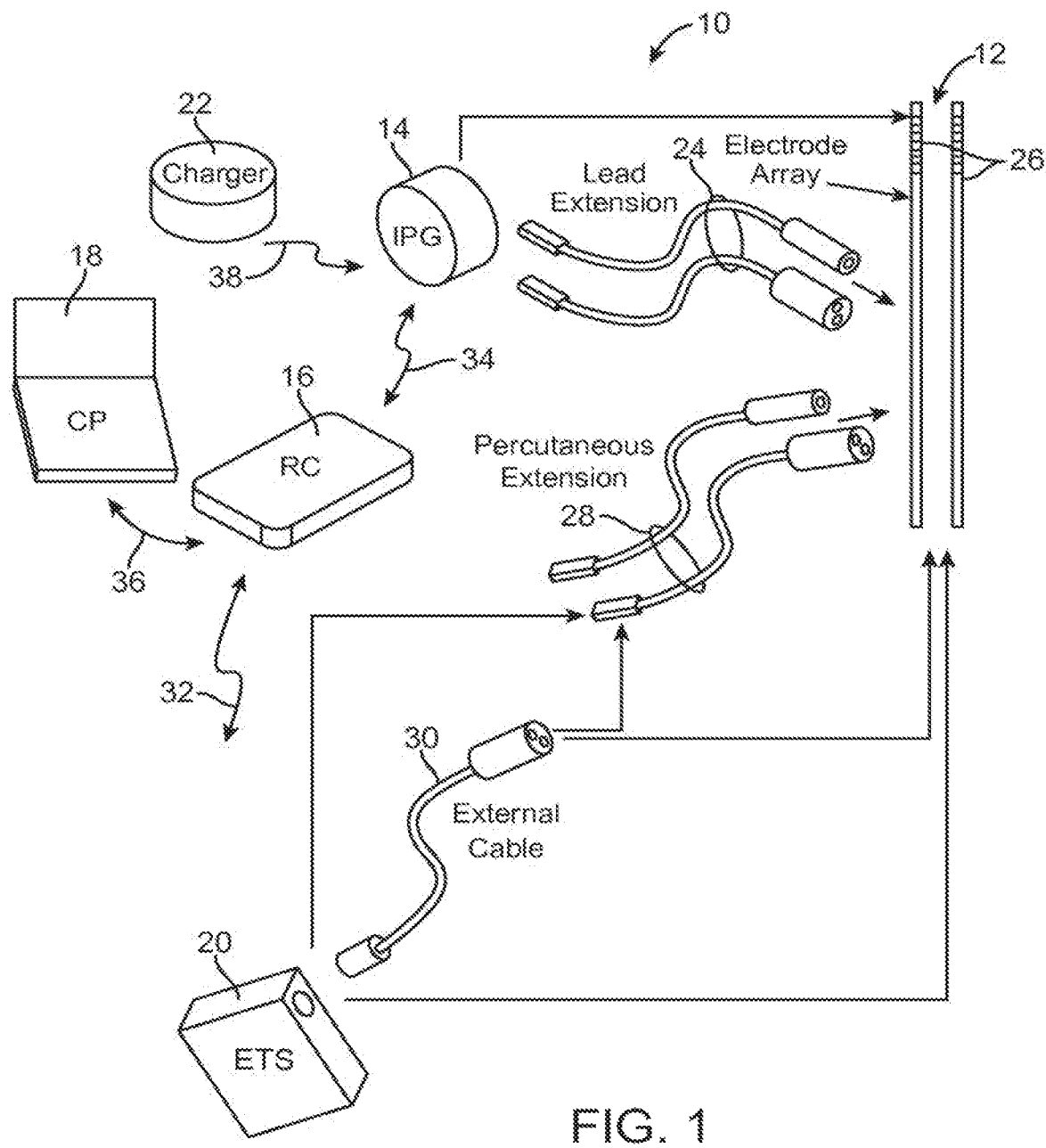
FIG. 1 is block diagram of a deep brain stimulation (DBS) system arranged in accordance with the present inventions.

Turning first to FIG. 1, an exemplary DBS neurostimulation system 10 generally includes at least one implantable stimulation lead 12 (in this case, two), a neurostimulator in the form of an implantable pulse generator (IPG) 14, an external remote controller RC 16, a clinician's programmer (CP) 18, an External Trial Stimulator (electrodes ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 may be arranged in-line along the neurostimulation leads 12. In alternative embodiments, the electrodes 26 may be arranged in a two-dimensional pattern on a single paddle lead if cortical brain stimulation is desired. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38.

For purposes of brevity, the details of the external charger 22 will not be described herein. Details of exemplary embodiments of external chargers are disclosed in U.S. Pat. No. 8,095,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
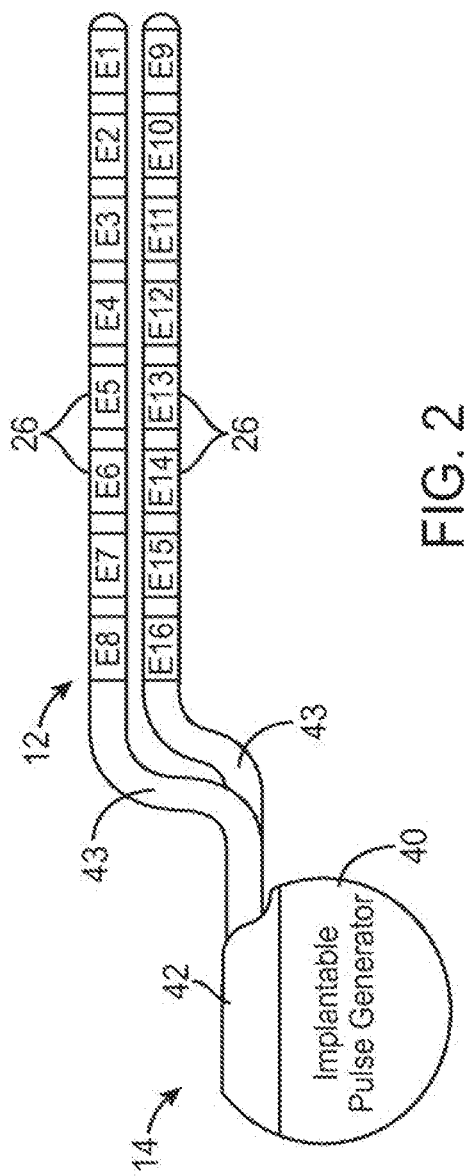
FIG. 2 is a plan view of an implantable pulse generator (IPG) and two percutaneous neurostimulation leads used in the DBS system of FIG. 1.

Referring to FIG. 2, the IPG 14 comprises an outer case 40 for housing the electronic and other components (described in further detail below), and a connector 42 to which the proximal end of the stimulation lead 12 mates in a manner that, electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

Each of the stimulation leads 12 comprises an elongated cylindrical lead body 43, and the electrodes 26 take the form of ring electrodes mounted around the lead body 43. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

As will be described in further detail below, the IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y). The IPG 14 may be capable of delivering the stimulation energy to the array 22 over multiple channels or over only a single channel.

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. Multipolar stimulation occurs when at least three of the lead electrodes 26 are activated, e.g., two as anodes and the remaining one as a cathode, or two as cathodes and the remaining one as an anode.

In the illustrated embodiment, IPG 14 can individually control the magnitude of electrical current flowing through each of the electrodes. In this case, it is preferred to have use current generators, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention.

Further details discussing the detailed structure and function of IPGs are described more fully in U.S. Pat. Nos. 6,516,227 and 6,993,384, which are expressly incorporated herein by reference.

Figure 3:
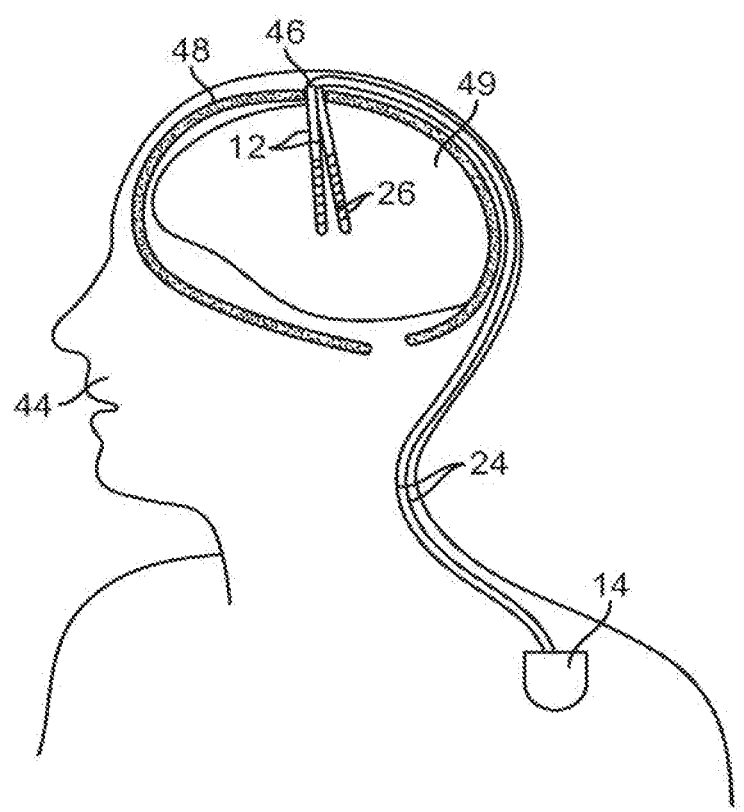
FIG. 3 is a plan view of the DBS system of FIG. 1 in use with a patient.

As shown in FIG. 3, two percutaneous neurostimulation leads 12 are introduced through a burr hole 46 (or alternatively, two respective burr holes) formed in the cranium 48 of a patient 44, and introduced into the parenchyma of the brain 49 of the patient 44 in a conventional manner, such that the electrodes 26 are adjacent a target tissue region, the stimulation of which will treat the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the neurostimulation leads 12 exit the burr hole 46, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the neurostimulation leads 12.

Figure 4:
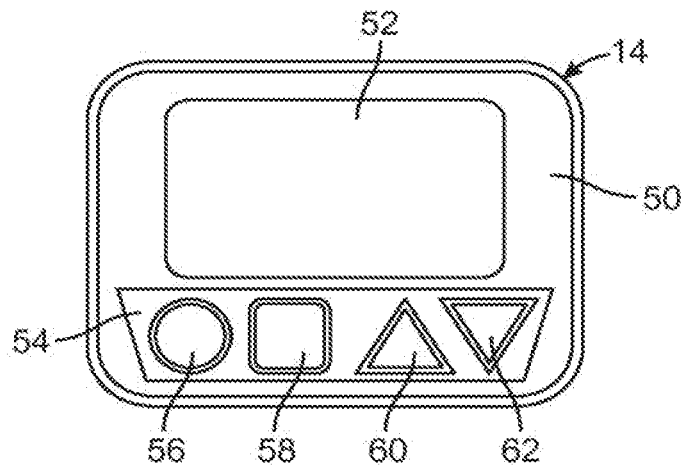
FIG. 4 is front view of a remote control (RC) used in the DBS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPS 14 to be turned ON and OFF, provide, for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can actuated to increment or decrement any of stimulation parameters of the pulse generated by the IPG 14, including pulse amplitude, pulse width, and pulse rate. For example, the selection button 58 can be actuated to place the RC 16 in an "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
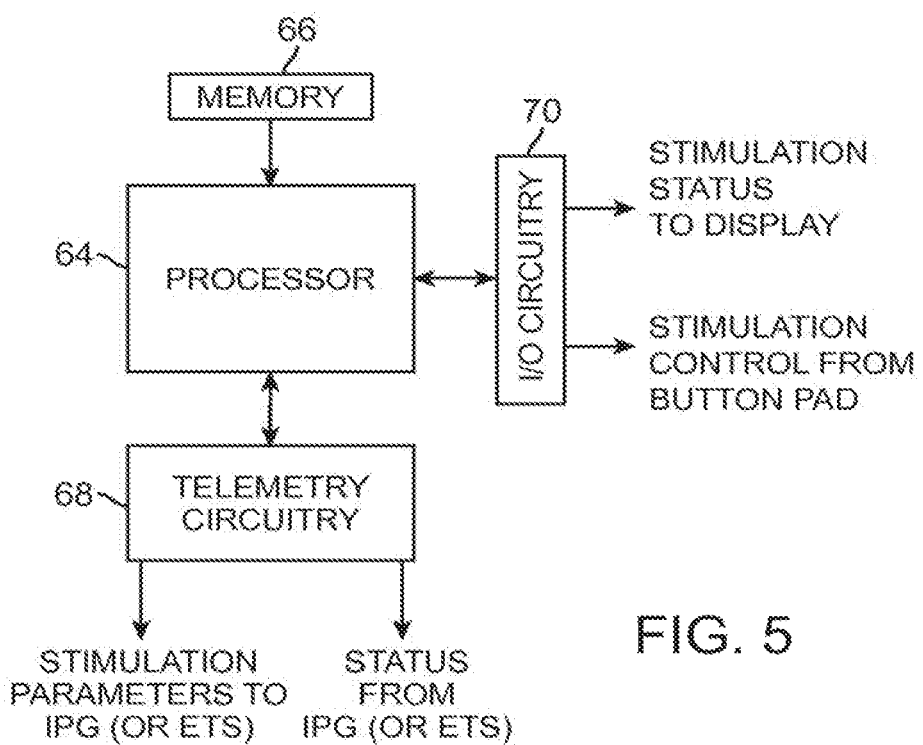
FIG. 5 is a block diagram of the internal components of the RC of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a look-up table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 (or ETS 20) via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 in the brain.

The overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), smartphone, etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

Figure 6:
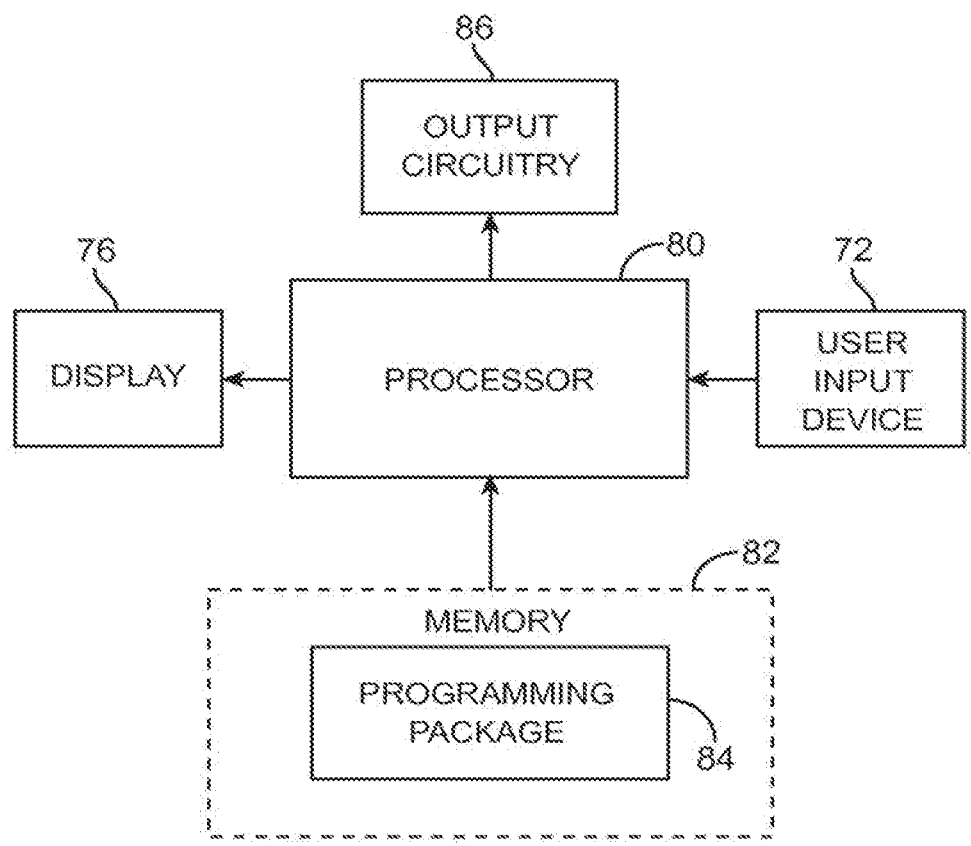
FIG. 6 is a block diagram of the internal components of a clinician's programmer (CP) used in the DBS system of FIG. 1.

Referring to FIG. 6, to allow the user to perform these functions, the CP 18 includes a standard user input device 72 (e.g., a keyboard, mouse, joystick, etc.) to allow a clinician to input information and control the process and a display monitor 76 housed in a case. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch. The CP 18 generally includes a processor 80 (e.g., a central processor unit (CPU)) and memory 82 that stores a stimulation programming package 84, which can be executed by the processor 80 to allow the user to program the IPG 14, and RC 16. The CP 18 further includes output circuitry 86 for downloading stimulation parameters to the IPG 14 and RC 16 and for uploading stimulation parameters already stored in the memory 66 of the RC 16, via the telemetry circuitry 68 of the RC 16.

Execution of the programming package 84 by the processor 80 provides a multitude of display screens (not shown) that can be navigated through via use of the user input device 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a therapeutic map (e.g., body regions targeted for therapy, body regions for minimization of side effects, along with metrics (e.g., Unified Parkinson's Disease Rating Scale (UPDRS)) of success for said targets) of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a more intuitive user interface that allows a user to visualize a resulting region of tissue activation in an animated fashion in response to changing the stimulation parameters.

Figure 7:
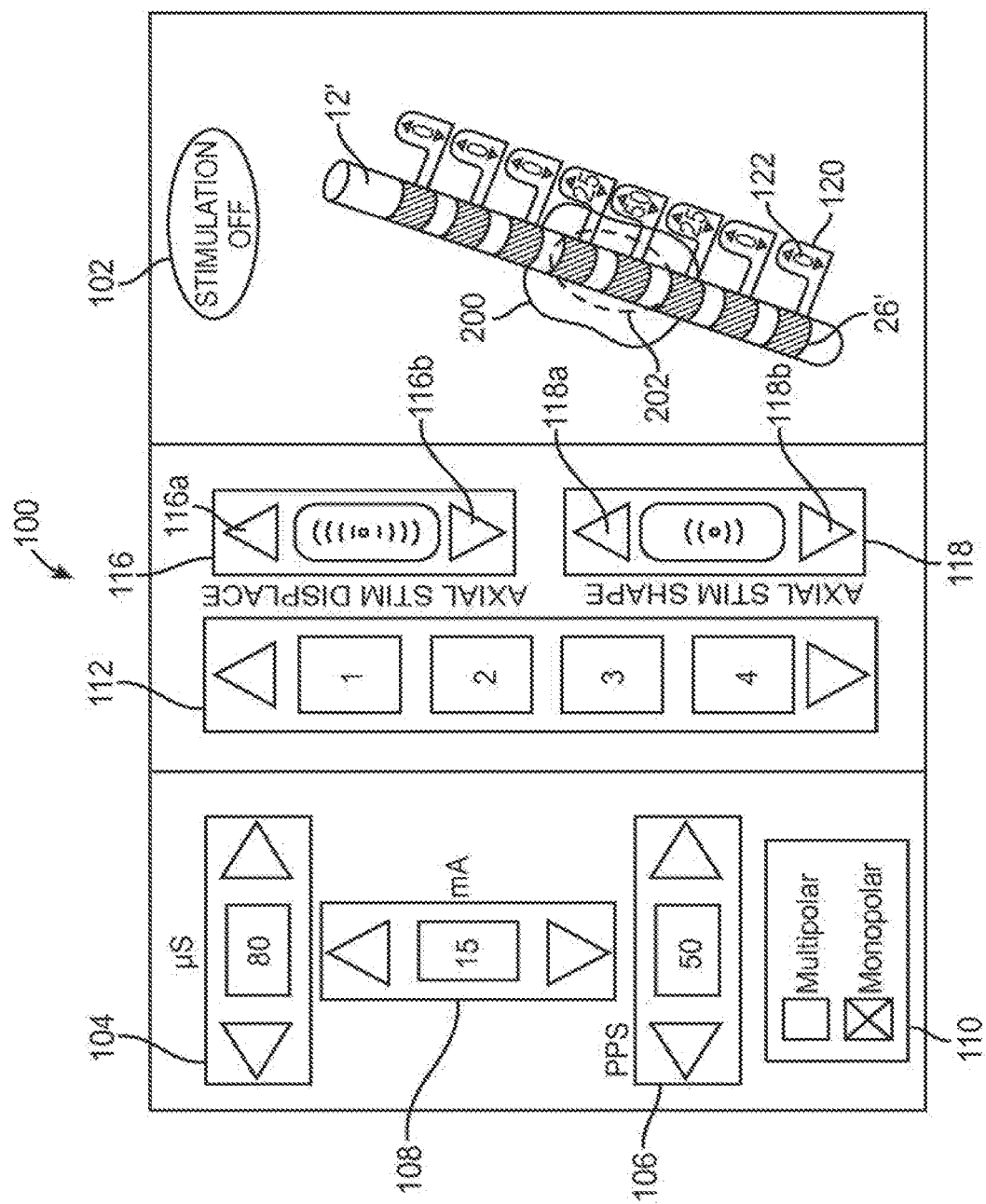
FIG. 7 is a plan view of a programming screen generated by the CP of FIG. 6.

In particular, a programming screen 100 can be generated by the CP 16, as shown in FIG. 7. The programming screen 100 allows a user to perform stimulation parameter testing. To this end, the programming screen 100 comprises a stimulation on/off control 102 that can be alternately clicked to turn the stimulation on or off. The programming screen 100 further includes various stimulation parameter controls that can be operated by the user to manually adjust stimulation parameters. In particular, the programming screen 100 includes a pulse width adjustment control 104 (expressed in microseconds (µs)), a pulse rate adjustment control 106 (expressed in pulses per second (pps), and a pulse amplitude adjustment control 108 (expressed in milliamperes (mA)). Each control includes a first arrow that can be clicked to decrease the value of the respective stimulation parameter and a second arrow that can be clicked to increase the value of the respective stimulation parameter. The programming screen 100 also includes multipolar/monopolar stimulation selection control 110, which includes check boxes that can be alternately clicked by the user to provide multipolar or monopolar stimulation. In an optional embodiment, the case 40 of the IPG 14 may be treated as one of the lead electrodes 26, such that both the case electrode 40 and at least one of the lead electrodes 26 can be used to convey anodic electrical current at the same time. Additionally, the case electrode may be configured with all the programmability of a lead electrode, with full anodic and cathodic fractionalization.

The programming screen 100 also includes an electrode combination control 112 having arrows that can be clicked by the user to select one of four different electrode combinations 1-4. Each of the electrode combinations 1-4 can be created using a variety of control elements.

The programming screen 100 also includes a set of axial electrical stimulation field displacement control elements 116 and a set of axial electrical stimulation field shaping control elements 118. In the illustrated embodiments, the control elements 116, 118, as well as the other control elements discussed herein, are implemented as a graphical icon that can be clicked with a mouse or touched with a finger in the case of a touchscreen. Alternatively, the control elements described herein may be implemented as a joy stick, touchpad, button pad, group of keyboard arrow keys, mouse, roller ball tracking device, horizontal or vertical rocker-type arm switches, etc., that can be pressed or otherwise moved to actuate the control elements.

When any of the axial electrical stimulation field displacement control elements 116 is actuated, control signals are generated in response to which the processor 80 is configured for generating stimulation parameter sets designed to axially displace the locus of the electrical stimulation field relative to the axis of the lead 12. Preferably, the control signals that are generated in response to the actuation of the control elements 116 or the alternative control elements are directional, meaning that the locus of the electrical stimulation field will be displaced in a defined direction in response to a continual actuation of a single control element irrespective of the current position of the locus electrical stimulation field locus. When any of the axial electrical stimulation field shaping control elements 118 is actuated, control signals are generated in response to which the processor 80 is configured for generating stimulation parameter sets designed to axially expand or contract the electrical stimulation field relative to its locus.

The control elements 116, 118 may be continually actuated (i.e., by continuously actuating one of the control elements 116, 118, e.g., by clicking on one of the control elements 116, 118 and holding the click (i.e., continuous actuation of the control following the initial "click"), or repeatedly actuating one of the control elements 116, 118, e.g., by repeatedly clicking and releasing one of the control elements 116, 118) to generate a series of control signals in response to which the processor 80 is configured for generating the plurality of stimulation parameter sets. The output telemetry circuitry 86 is configured for transmitting these stimulation parameters sets to the IPG 14.

Each of the sets of control elements 116, 118 takes the form of a double arrow (i.e., two oppositely pointing control element arrows) that can be actuated to modify the electrical stimulation field depending on the mode of operation. For example, an upper arrow control element 116*a* can be clicked to axially displace the locus of the electrical stimulation field (i.e., along the axis of the lead 12) in the proximal direction; a lower arrow control element 116*b* can be clicked to axially displace the locus of the electrical stimulation field (i.e., along the axis of the lead 12) in the distal direction; a lower arrow control element 118*a* can be clicked to axially contract the electrical stimulation field about its locus, and an upper arrow control element 118*b* can be clicked to axially expand the electrical stimulation field about its locus.

The locus of the electrical stimulation field may be displaced, e.g., by gradually "steering" or shifting electrical current between electrodes in a single timing channel. For example, the locus of the electrical stimulation field can be gradually displaced axially in the distal direction along the lead 12 by gradually including electrodes in a stimulating electrode group and gradually excluding other electrodes from the stimulating electrode group in the single timing channel.

The locus of the electrical stimulation field may alternatively be displaced using multiple timing channels. In particular, the electrical energy can be conveyed between different combinations of electrodes in accordance with multiple timing channels; that is, a first stimulating electrode group can be used during a first timing channel, a second stimulating electrode group can be used during a second timing channel, and so forth, and the groups may or may not overlap. The magnitude of the electrical energy conveyed in accordance with at least one of the multiple timing channels can be modified to effectively displace the locus of the stimulation region as experienced by the patient.

The electrical stimulation field can be expanded and contracted by gradually "steering" or shifting electrical current between electrodes in a similar manner described above with respect to the displacement of the locus of the electrical stimulation field, with the exception that the electrical stimulation field is expanded or contracted.

For example, the electrical stimulation field can be gradually expanded axially along the lead 12 by gradually including electrodes in a stimulating electrode group, and can be gradually contracted axially along the lead 12 by gradually excluding electrodes in a stimulating electrode group. The electrical stimulation field can be alternatively expanded and contracted using multiple timing channels in a similar manner described above with respect to the displacement of the locus of the electrical stimulation field, with the exception that the electrical stimulation field is expanded or contracted. For example, the magnitude of the electrical energy conveyed in accordance with at least one of the multiple timing channels can be modified to effectively expand or contract the stimulation field.

Further details discussing different techniques for modifying an electrical stimulation field is disclosed in U.S. Provisional Patent Application 61/374,879, entitled "User Interface for Segmented Neurostimulation Leads," which is expressly incorporated herein by reference. In an optional embodiment, additional control elements can be provided to circumferentially displace the locus of the electrical stimulation field, circumferentially contract or expand the electrical stimulation field, radially displace the locus of the electrical field, or radially contract or expand the electrical stimulation field, as disclosed in U.S. Provisional Patent Application 61/374,879.

Although the programming screen 100 illustrates only one neurostimulation lead 12 with electrodes arranged in only one dimension, thereby allowing the electrical current to only be steered in one dimension, it should be appreciated that the programming screen 100 may additionally illustrate the other neurostimulation lead 12, thereby arranging the electrodes in two dimensions and allowing the electrical current to be steered in two dimensions. In this case, using appropriate control elements (e.g., left and right arrows), the locus of the electrical stimulation field can be displaced in the transverse direction (perpendicular to the axial direction, and in this case, left or right) and/or the electrical stimulation-field can be expanded or contracted in the transverse direction. Of course, the electrodes can be arranged in three-dimensions (e.g., by arranging three neurostimulation leads in three-dimensions or by using electrodes on a single neurostimulation lead that are arranged in three-dimensions, e.g., the segmented neurostimulation leads described in U.S. Provisional Patent Application Ser. No. 61/374,879), in which case, the electrical current can be steering in three-dimensions.

The programming screen 100 displays three-dimensional graphical renderings of the lead 12' and electrodes 26'. In an optional embodiment, iconic control elements 120 are graphically linked to the three-dimensional electrode renderings 26'. Continual actuation of the control elements 120 generates control signals that prompt the processor 80 to generate stimulation parameters designed to modify the electrical stimulation field, which stimulation parameters are then transmitted from the output circuitry 86 of the CP 18 to the IPG 14. In the illustrated embodiment, each of the control elements 120 has an up arrow and a down arrow that can be respectively actuated (e.g., by clicking) to respectively increase or decrease the electrical current flowing through the electrode 26 corresponding to the graphical electrode rendering 26' to which the actuated control element 120 is graphically linked.

Actuation of any of the control elements 120 essentially steers electrical current from other active electrodes to the electrode associated with the actuated control element 120 or from the electrode associated with the actuated control element 120 to other active electrodes. In this manner, the locus of the electrical stimulation field can be displaced, the shape of the electrical stimulation field can be modified, and if two separate electrical stimulation fields current exist, electrical current can be shifted from one of the electrical stimulation fields (effectively decreasing its size) to another of the electrical stimulation fields (effectively increasing its size).

The control element 120 also includes an indicator 122 that provides an indication of the amount of electrical current flowing through each of the electrodes 26 in terms of a fractionalized current value. The indicators 122 may perform this function when the respective control elements 120 are actuated or when the axial electrical stimulation field displacement control elements 116 and axial electrical stimulation field shaping control elements 118 are actuated.

The programming screen 100 displays the three-dimensional graphical renderings of the lead 12' and electrodes 26' relative to a graphical representation of the anatomical structure 200 that is preferably the stimulation target. For example, if the DBS indication is Parkinson's disease, the anatomical structure is preferably the subthalamic nucleus (STN) or the globus pallidus (GPi). If the DBS indication is Essential Tremor, the anatomical structure is preferably the thalamus. If the DBS indication is depression, the anatomical structure is one or more of the nucleus acumbens, ventral striatum, ventral capsule, anterior capsule, or the Brodmann's area 25. If the DBS indication is epilepsy, the anatomical structure is preferably the anterior nucleus. If the DBS indication is a gait disorder, the anatomical structure is preferably the pedunculoponfine (PPN). If the DBS indication is dementia, Alzheimer's disease or memory disorders, the anatomical structure is preferably anywhere in the Papez circuit. The anatomical structure can be obtained from any available brain atlas, or from a patient specific brain atlas derived from, e.g., a magnetic resonant Imager (MRI), computed tomography (CT); X-ray, fluoroscopy, ventriculography, ultrasound, or any other imaging modality or a merging of any or all of these modalities.

Based on the current stimulation parameter-set, the processor 80 computes an estimate of a resulting region of tissue activation (RTA), and generates display signals that prompt the monitor 76 to display a graphical representation of the RTA 202 with the graphical lead 12' and graphical anatomical structure 200. In the preferred embodiment, the graphical RTA 202 is superimposed over the graphical anatomical structure 200. In the illustrated embodiment, although the graphical lead 12', graphical anatomical structure 200, and the graphical RTA 202 are displayed in an oblique view, they can be alternatively displayed in any one or more of traditional planes of section axial, coronal, and sagittal). Further details discussing technique for computing the estimate of a RTA are disclosed in A. M. M. Frankemolle, et al., *Reversing Cognitive-Motor Impairments in Parkinson's Disease Patients Using a Computational Modelling Approach to Deep Brain Stimulation Programming*, Brain 2010; pp. 1-16), which is expressly incorporated herein by reference.

Significantly, the processor 80 is capable of generating the display signals in response to a series of stimulation parameter sets defined in the programming screen 100 in a manner that prompts the monitor 76 to animate the graphical RTA 202. For the purposes of this specification to "animate" or "animation" means that the user perceives a movement or change in the graphical RTA 202 in a continuous or near-continuous (flickering) manner.

Figure 8:
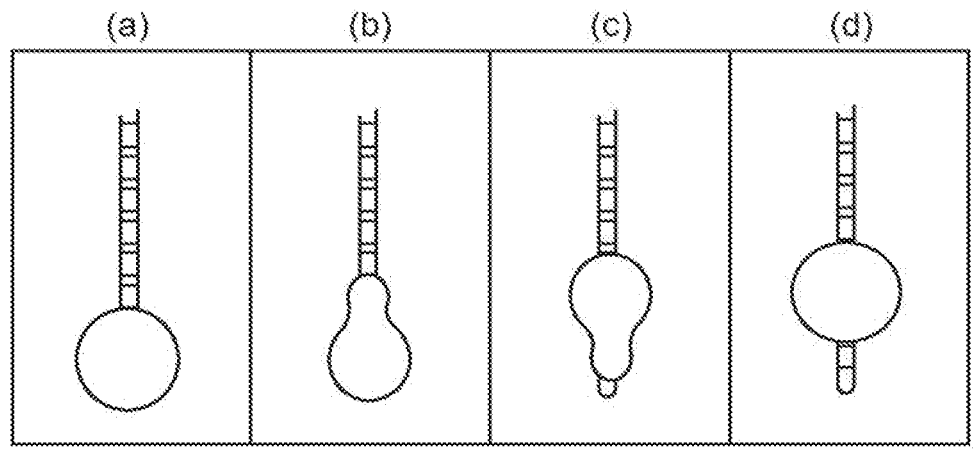
FIG. 8 is a plan view of the animation of the shape change of a region of tissue activation computed by the CP of FIG. 6.

For example, the shape of the graphical RTA 202 may be gradually modified, as illustrated in FIG. 8. In this case, the shape of the graphical RTA 202 begins as an oval (FIG. 8*a*), then a pear shape that is fattened at the bottom (FIG. 8*b*), then a pear shape that is fattened at the top (FIG. 8*c*), and finally back to an oval that is proximally displaced from the initial oval (FIG. 8*d*).

Figure 9:
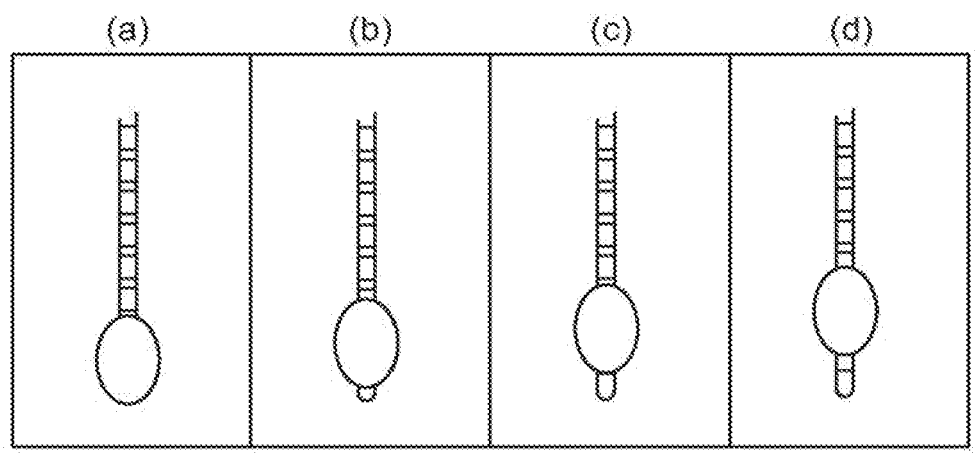
FIG. 9 is a plan view of the animation of the displacement change of a region of tissue activation computed by the CP of FIG. 6.

As another example, the locus position of the graphical RTA 202 may be displaced without changing shape, as illustrated in FIG. 9. In this case, the locus of the oval graphical RTA 202 is displaced from its initial distal position (FIG. 9*a*) to a more proximal position (FIG. 9*b*), to a more proximal position (FIG. 9*c*), to an even more proximal position (FIG. 9*d*).

As still another example, the electrical current can be shifted between a proximal region and a distal region of the graphical RTA 202, such that the size of the distal region is relatively small and the size of the proximal region is relatively large (FIG. 10*a*), then the size of the distal region gets larger and the size of the proximal region gets smaller (FIG. 10*b*), then the size of the distal region gets even larger and the size of the proximal region gets even smaller (FIG. 10*c*), and then the size of the distal region gets even larger and the size of the proximal region gets even smaller, such that the size of the distal region ends up relatively large and the size of the proximal region ends up relatively small (FIG. 10*d*).

Figure 10:
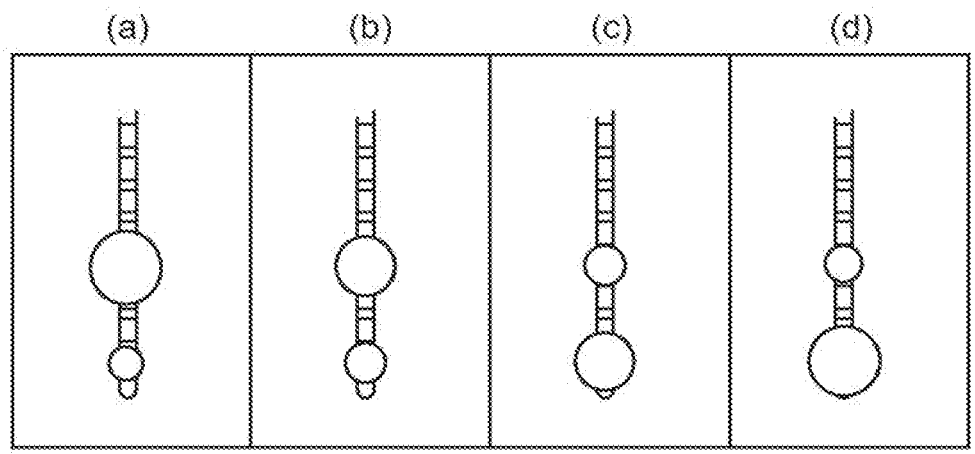
FIG. 10 is a plan view of the animation of the size change of a region of tissue activation computed by the CP of FIG. 6.

Other animated features for the graphical RTA 202 include displaying the intensity of the graphical RTA. 202 in different shades (e.g., modifying the shade of the graphical RTA 202 from light green to dark green its intensity increases), displaying the intensity of the graphical RTA 202 in different transparencies (e.g., the transparency of the graphical RTA 202 decreases as its intensity increases), or displaying the intensity of the graphical RTA 202 in different colors (e.g., from green to blue, to orange, to red, etc. as its intensity increases). These additional features can be combined with the previous animated features related to the shape change of the graphical RTA 202 (FIG. 8), the displacement of the locus of the graphical RTA 202 (FIG. 9), and/or the shifting of current from one region of the graphical RTA 202 to another region of the graphical RTA 202 (FIG. 10). Although the RTA 202 has been illustrated above in a two-dimensional manner, the RTA 202 is preferably illustrated in a three-dimensional manner.

For example, with reference to FIGS. 11a-11j, a graphical RTA 202 is displayed in a three-dimensional animated manner as electrical current is steered up the electrodes 26 of the neurostimulation lead 12. As there illustrated, the RTA 202 expands, contracts, and it is displaced up the neurostimulation lead 12 as electrical current is steered along the electrodes 26 (as represented by a column of eight boxes on the left side of the figures) in a monopolar manner. Essentially, the RTA 202 graphically appears to "inch-worm" itself up the neurostimulation lead 12.

Figure 11A:
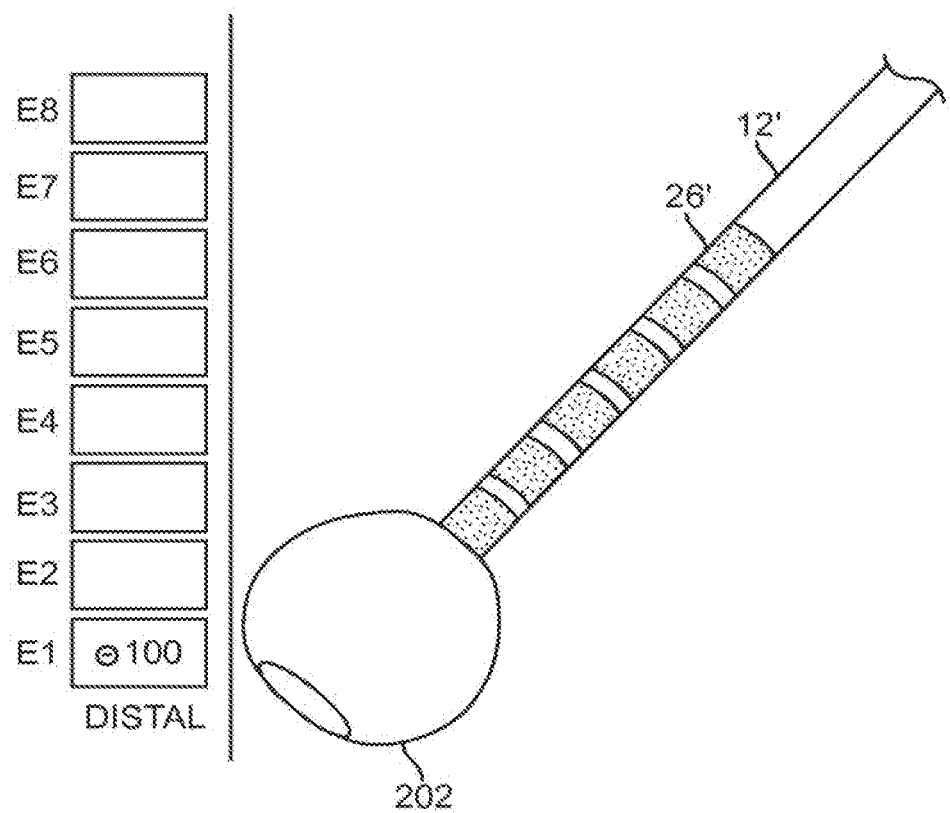
FIGS. 11*a*-11*j* are plan views of the animation of a region of tissue activation computed by the CP of FIG. 6 as electrical current is steered up a neurostimulation lead.
Figure 11B:
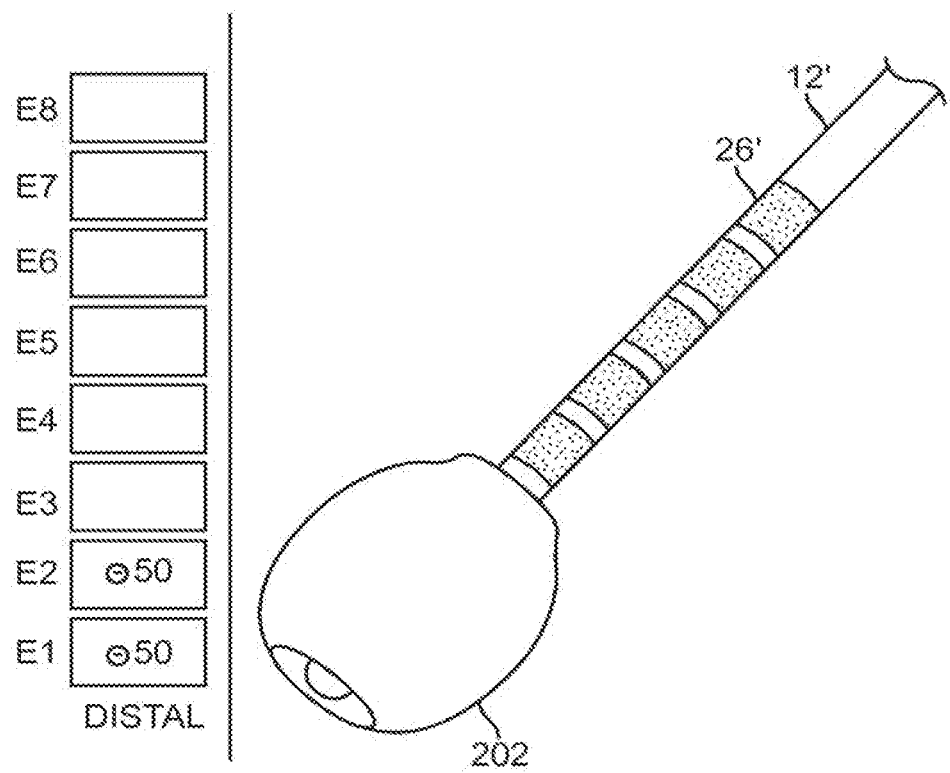
Figure 11C:
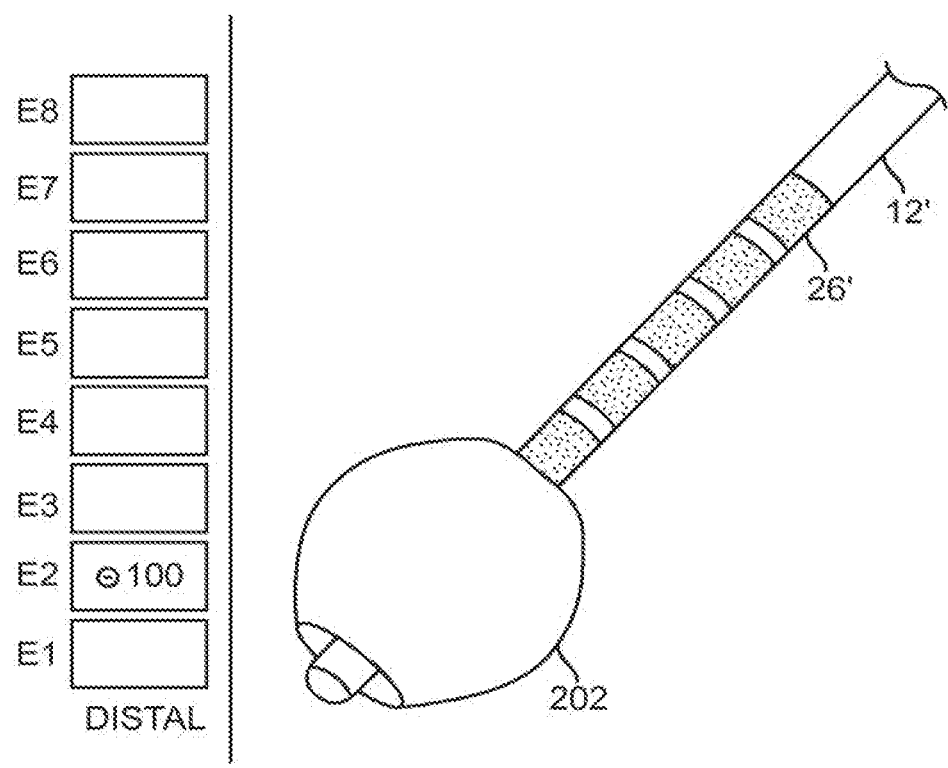
Figure 11D:
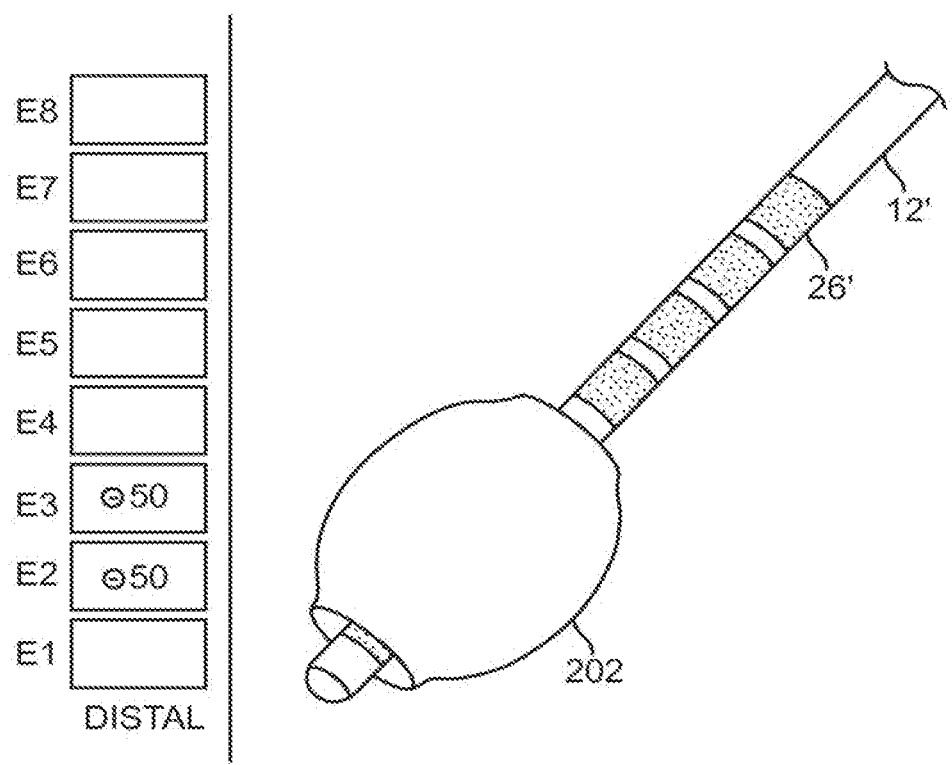
Figure 11E:
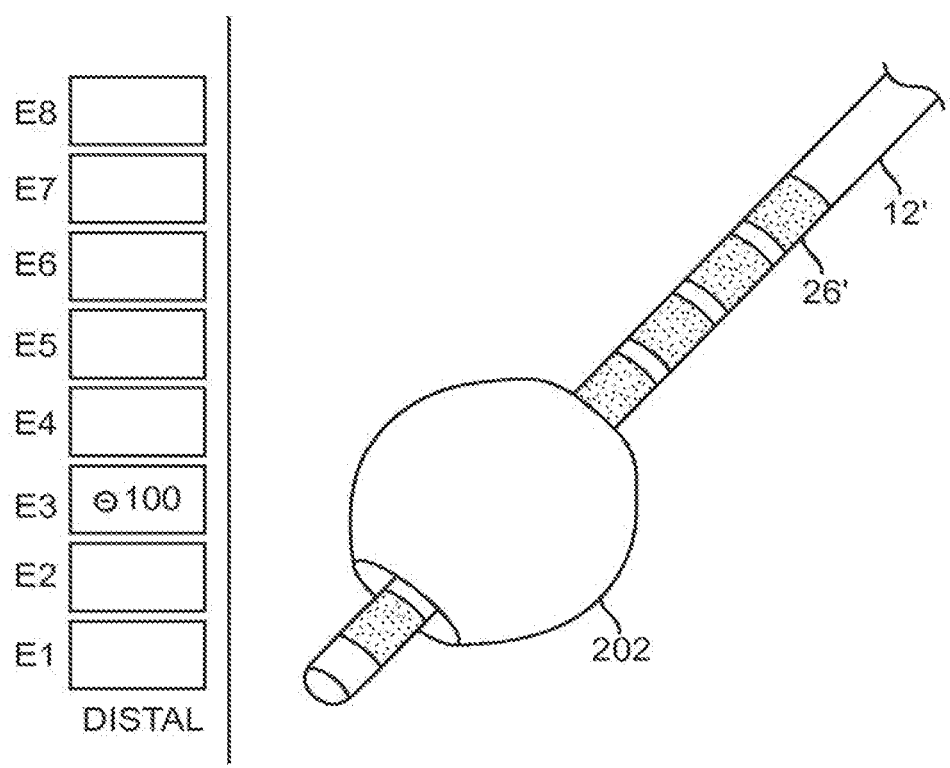
Figure 11F:
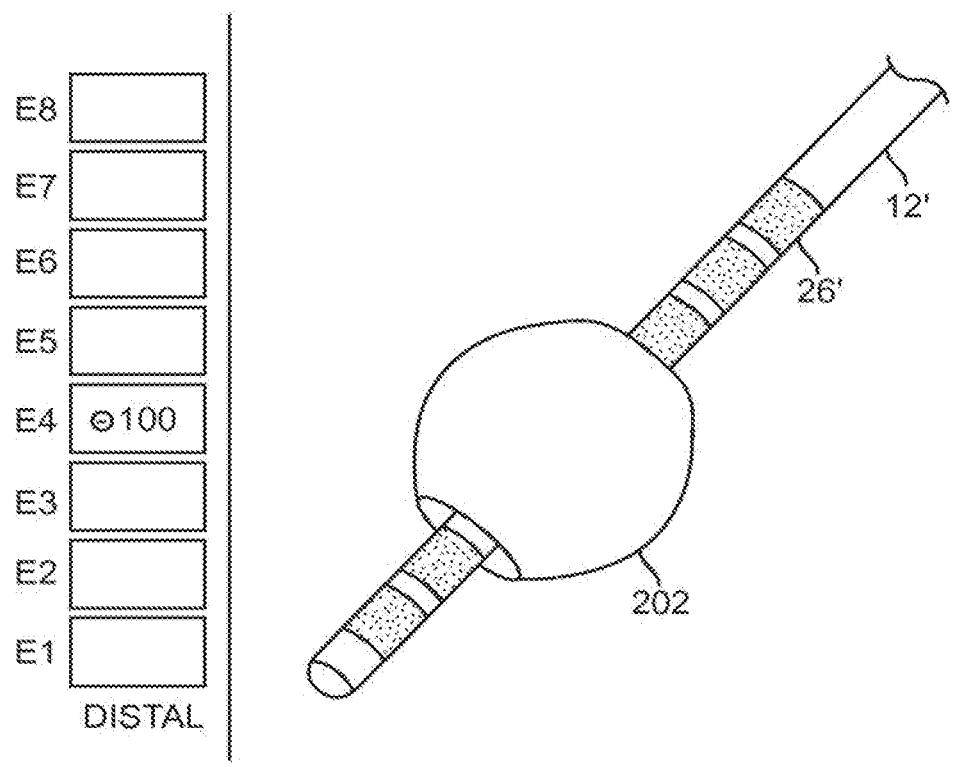
Figure 11G:
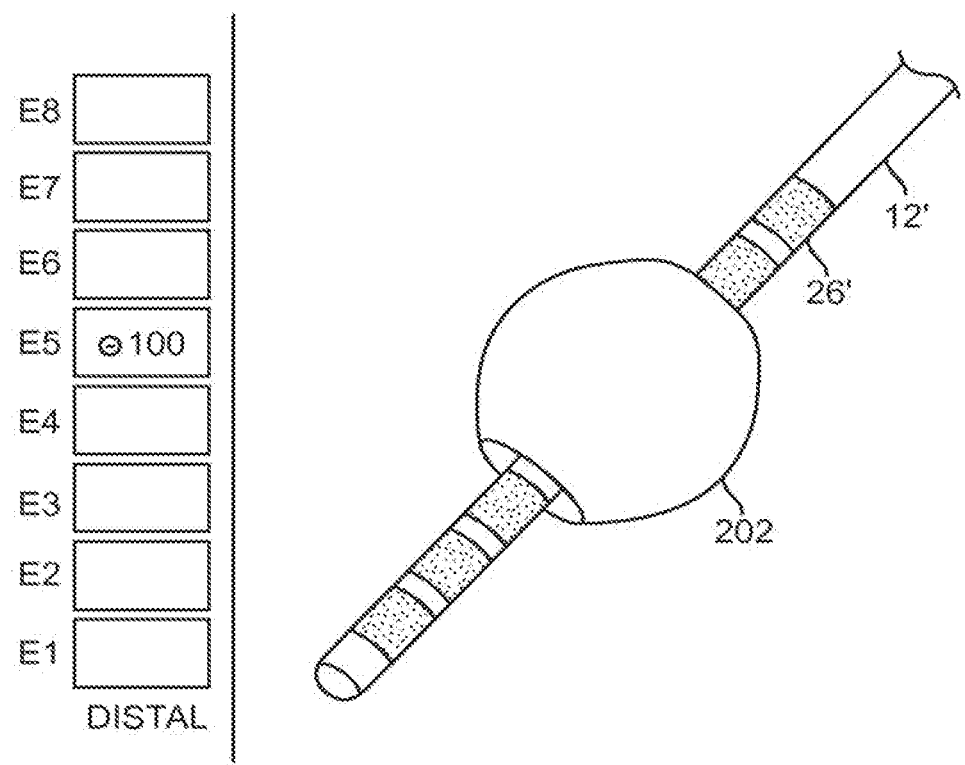
Figure 11H:
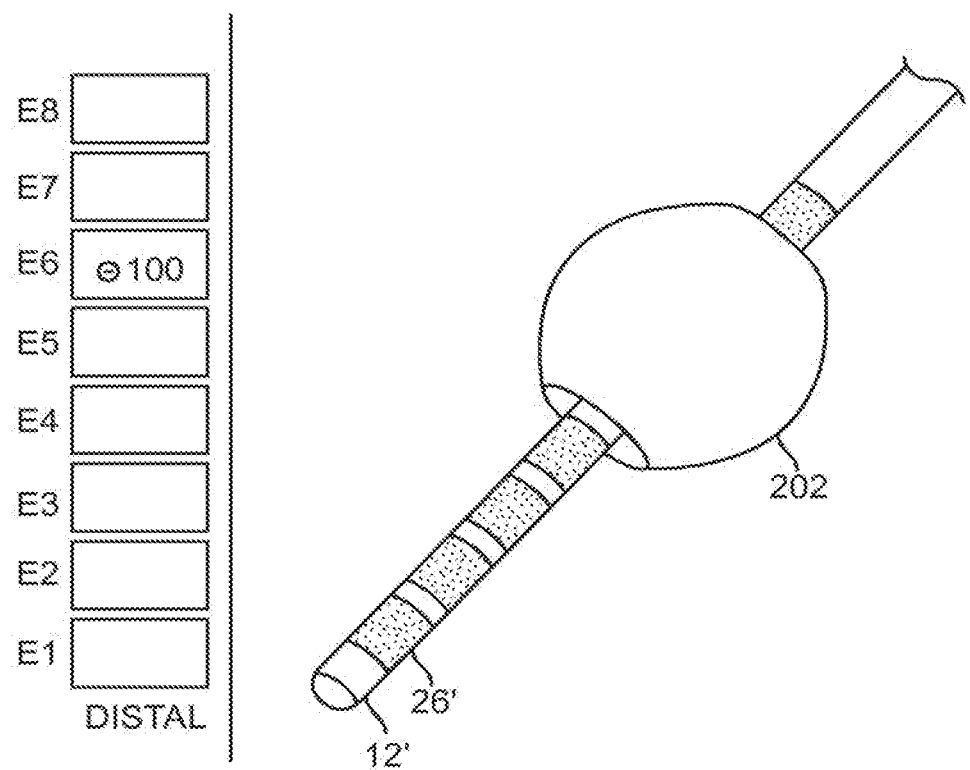
Figure 11I:
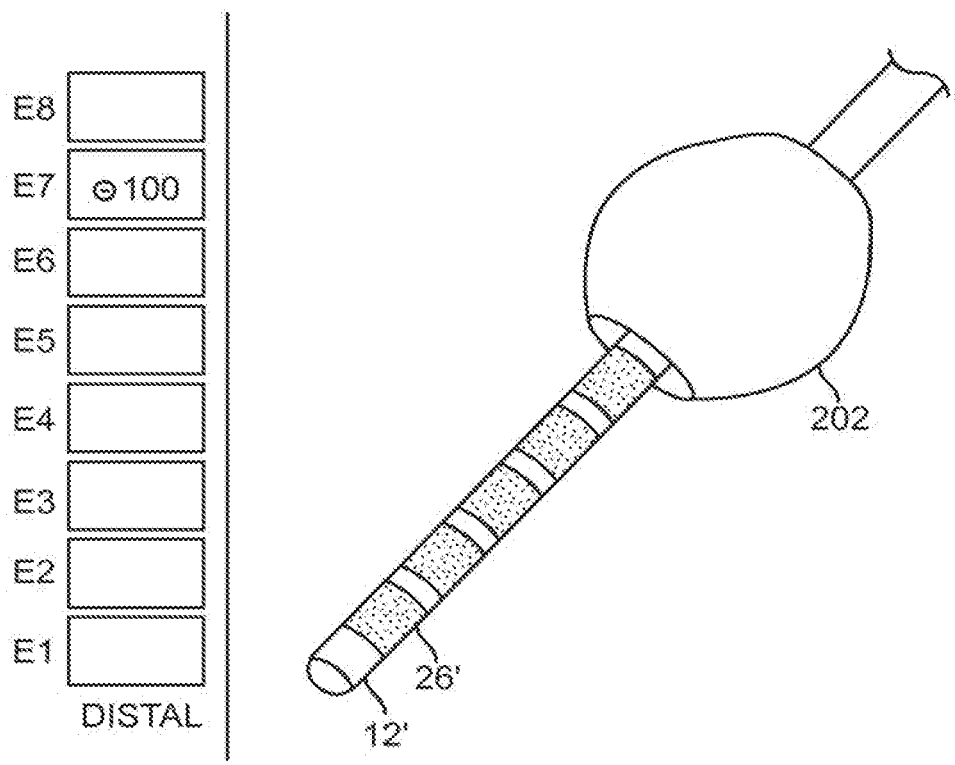
Figure 11J:
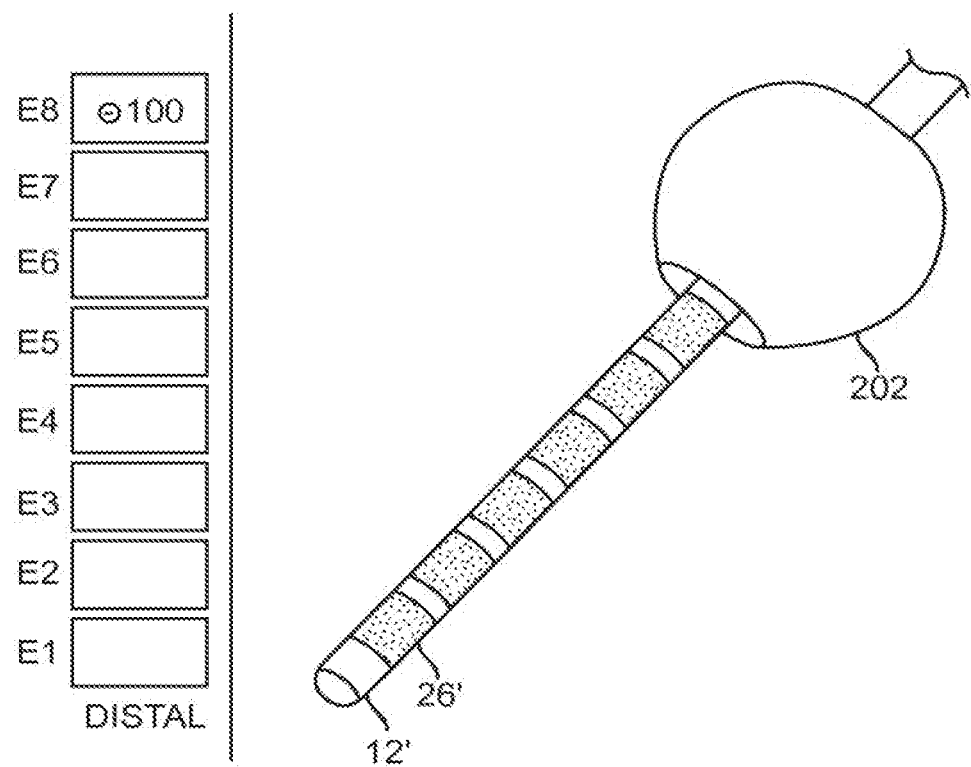

For example, when electrode E1 has 100% of the cathodic current, the graphical RTA 202 is at its distal-most point and is axially contracted (FIG. 11a). When electrodes E1 and E2 each has 50% of the cathodic current, the RTA 202 axially expands in the proximal direction (FIG. 11b). When electrode E2 has 100% of the cathodic current, the RTA 202 axially contracts in the proximal direction (FIG. 11c), essentially displacing the RTA 202 from its initial position to a more proximal position. When electrodes E2 and E3 each has 50% of the cathodic current, the RTA 202 axially expands in the proximal direction (FIG. 11d), and when electrode E3 has 100% of the cathodic current, the RTA 202 axially contracts in the proximal direction (FIG. 11e), essentially displacing the RTA 202 from to an even more proximal position. These "inch worming" steps can be repeated to displace the RTA 202 to even more proximal positions (FIGS. 11f-11j).

Although the foregoing techniques have been described as being implemented in the CP 18, it should be noted that this technique may be alternatively or additionally implemented in the RC 16. Furthermore, the RTA simulation and display techniques described herein may be performed in a stand-alone manner (i.e., using a computer that does not program the IPG 14). For example, a conventional computer can be used to stimulate and graphically display the RTA in an animated fashion, and a programmer can be used to program the IPG 14 with stimulation parameters obtained from the conventional computer.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system for programming an electrical tissue stimulator coupled to an array of electrodes, comprising:
   a display screen; and
   at least one processor configured for
      receiving a user input of a modification of a stimulation parameter set that, when applied to the electrodes, will shift electrical current between the electrodes to modify a region of tissue activation,
      in response to the user input of the modification, automatically computing an estimate of the modified region of tissue activation based on the modification of the stimulation parameter set, and
      in response to the user input of the modification and the computing of the estimate, automatically generating display signals capable of prompting the display screen to display an animated graphical representation of a shift of the region of tissue activation to the computed estimate of the modified region of tissue activation such that the user perceives the modification of the stimulation parameter set as movement, in a continuous or flickering manner, of the region of tissue activation through a series of intermediate depictions to the computed estimate of the modified region of tissue activation.

2. The system of claim 1, further comprising an input device for providing the user input.

3. The system of claim 2, wherein the input device comprises at least one of a graphical arrow, a joystick, a touchpad, a button pad, a group of keyboard arrow keys, a mouse, a roller ball tracking device, or horizontal or vertical rocker-type arm switches.

4. The system of claim 1, wherein the at least one processor is configured to change a shape of the region of tissue activation during the shift.

5. The system of claim 1, wherein the at least one processor is configured to change a locus position of the region of tissue activation during the shift.

6. The system of claim 1, wherein the at least one processor is configured to change a size of the region of tissue activation during the shift.

7. The system of claim 1, wherein the at least one processor is configured to change a shade of the region of tissue activation during the shift.

8. The system of claim 1, wherein the at least one processor is configured to change a transparency of the region of tissue activation during the shift.

9. The system of claim 1, wherein the at least one processor is configured to change a color of the region of tissue activation during the shift.

10. The system of claim 1, wherein the animated graphical representation is displayed as being three-dimensional.

11. The system of claim 1, wherein the stimulation parameter set comprises an electrode combination.

12. The system of claim 11, wherein the electrode combination is a fractionalized electrode combination.

13. A non-transitory memory having stored thereon, for execution by a processor, a program for programming an electrical tissue stimulator coupled to an array of electrodes, the program comprising:
   receiving, by the processor, a user input of a modification of a stimulation parameter set that, when applied to the electrodes, will shift electrical current between the electrodes to modify a region of tissue activation;
   in response to the user input of the modification, automatically computing, by the processor, an estimate of the modified region of tissue activation based on the modification of the stimulation parameter set; and
   in response to the user input of the modification and the computing of the estimate, automatically generating, by the processor, display signals capable of prompting a display screen to display an animated graphical representation of a shift of the region of tissue activation to the computed estimate of the modified region of tissue activation such that the user perceives the modification of the stimulation parameter set as movement, in a continuous or flickering manner, of the region of tissue activation through a series of intermediate depictions to the computed estimate of the modified region of tissue activation.

14. The non-transitory memory of claim 13, wherein the shift of the region of tissue activation changes a shape of the region of tissue activation.

15. The non-transitory memory of claim 13, wherein the shift of the region of tissue activation changes a locus position of the region of tissue activation.

16. The non-transitory memory of claim 13, wherein the shift of the region of tissue activation changes a size of the region of tissue activation.

17. A method for programming an electrical tissue stimulator coupled to an array of electrodes, the method comprising:
   receiving, by a processor, a user input of a modification of a stimulation parameter set that, when applied to the electrodes, will shift electrical current between the electrodes to modify a region of tissue activation;
   in response to the user input of the modification, automatically computing, by the processor, an estimate of the modified region of tissue activation based on the modification of the stimulation parameter set; and
   in response to the user input of the modification and the computing of the estimate, automatically generating, by the processor, display signals capable of prompting a display screen to display an animated graphical representation of a shift of the region of tissue activation to the computed estimate of the modified region of tissue activation such that the user perceives the modification of the stimulation parameter set as movement, in a continuous or flickering manner, of the region of tissue activation through a series of intermediate depictions to the computed estimate of the modified region of tissue activation.

18. The method of claim 17, wherein the shift of the region of tissue activation changes a shape of the region of tissue activation.

19. The method of claim 17, wherein the shift of the region of tissue activation changes a locus position of the region of tissue activation.

20. The method of claim 17, wherein the shift of the region of tissue activation changes a size of the region of tissue activation.

* * * * *